United States Patent [19]

Nabata

[11] Patent Number: 5,300,650
[45] Date of Patent: Apr. 5, 1994

[54] PROCESS FOR PRODUCING AMINOMETHYLPYRIDINE HAVING A CHLORINE ATOM AT α-POSITION

[75] Inventor: Toshinari Nabata, Hyogo, Japan

[73] Assignee: Koei Chemical Co., Ltd., Osaka, Japan

[21] Appl. No.: 927,425

[22] PCT Filed: Jan. 31, 1992

[86] PCT No.: PCT/JP92/00094

§ 371 Date: Sep. 25, 1992

§ 102(e) Date: Sep. 25, 1992

[87] PCT Pub. No.: WO92/13840

PCT Pub. Date: Aug. 20, 1992

[30] Foreign Application Priority Data

Feb. 4, 1991 [JP] Japan .................................. 3-035598

[51] Int. Cl.$^5$ .......................................... C07D 213/61
[52] U.S. Cl. .................................................. 546/329
[58] Field of Search ......................................... 546/329

[56] References Cited

FOREIGN PATENT DOCUMENTS 49-24969  3/1974  Japan .................................. 546/329

Primary Examiner—Alan L. Rotman
Assistant Examiner—Zinna N. Davis
Attorney, Agent, or Firm—Stevens, Davis, Miller & Mosher

[57] ABSTRACT

A process for producing an aminomethylpyridine having a chlorine atom at the α-position, for example, 2-chloro-5-aminomethylpyridine by subjecting a cyanopyridine having a chlorine atom at the α-position, for example, 2-chloro-5-cyanopyridine, to a catalytic reduction in the presence of a tertiary amine in a non-aqueous reaction system.

With the process, the removal of the chlorine atom bonding to the α-position can be depressed and an aminomethylpyridine having a chlorine atom at the α-position can be produced at a high yield.

10 Claims, No Drawings

PROCESS FOR PRODUCING AMINOMETHYLPYRIDINE HAVING A CHLORINE ATOM AT α-POSITION

INDUSTRIAL FIELD OF UTILIZATION

The present invention relates to a process for producing an aminomethylpyridine having a chlorine atom at the α-position. The aminomethylpyridine having a chlorine atom at the α-position is a compound which is useful as a raw material for synthesis of medicines, agricultural chemicals, etc.

PRIOR ART

For production of an aminomethylpyridine having a chlorine atom at the α-position, there has example, 2-chloro-5-cyanopyridine to a catalytic reduction using a Raney nickel in the presence of ammonia, water and, as necessary, an organic solvent to produce 2-chloro-5-aminomethylpyridine (DT Laid-Open Publication No. 3726933).

PROBLEMS TO BE SOLVED BY THE INVENTION

In the above conventional process, however, the yield of desired product is about 50% as shown in Comparative Example described later, and is not sufficiently high; thus, said process is not satisfactory as an industrial process.

The object of the present invention is to provide a process for producing an aminomethylpyridine having a chlorine atom at the α-position, at a high yield as compared with the conventional processes.

MEANS FOR SOLVING THE PROBLEMS

In order to improve the conventional processes, the present inventor paid attention to aminomethylpyridine which is produced in a large amount as a by-product in said process (reference can be made to Comparative Example described later). In view of the fact that a chlorine atom bonding to the α-position of pyridine nucleus is very active generally, the present inventor assumed that the above aminomethylpyridine as by-product is formed as a result of removal of a chlorine atom at the α-position under the catalytic reduction conditions employed.

Hence, the present inventor made research on a method capable of depressing the reaction for the above removal of chlorine atom (dechlorination). As a result, it was surprisingly found the fact that the removal of a chlorine atom at the α-position and other side reactions are depressed by subjecting a starting material, i.e., a cyanopyridine having a chlorine atom at the α-position, to a catalytic reduction in the presence of a hydrogenation catalyst in a non-aqueous reaction system and thereby the yield of desired product, i.e., an aminomethylpyridine having a chlorine atom at the α-position can be increased. The finding has led to the completion of the present invention.

The present inventor made further study. As a result, it was found the fact that the removal of a chlorine atom at the α-position atom and other side reactions are depressed more preferably by subjecting a cyanopyridine having a chlorine atom at the α-position, to a catalytic reduction with a tertiary amine being allowed to coexist in the reaction system and thereby the yield of a desired product, i.e., an aminomethylpyridine having a chlorine atom at the α-position can be increased further. The finding has led to the completion of the present invention.

The present invention relates to a process for producing an aminomethylpyridine having a chlorine atom at the α-position in the pyridine nucleus by subjecting a starting material, i.e., a cyanopyridine having a chlorine atom at the α-position, to a catalytic reduction in the presence of a hydrogenation catalyst, which process is characterized in that said cyanopyridine is subjected to a catalytic reduction in an non-aqueous reaction system, as well as to a process for producing an aminomethylpyridine having a chlorine atom at the α-position in the pyridine nucleus by subjecting a cyanopyridine having a chlorine atom at the α-position, to a catalytic reduction in the presence of a hydrogenation catalyst, which process is characterized in that said cyanopyridine is subjected to a catalytic reduction with a tertiary amine being allowed to coexist in the reaction system.

As to the cyanopyridine having a chlorine atom at the α-position, used as a starting material in the Present invention, there are mentioned, for example, 2-chlorocyanopyridine represented by general formula (I)

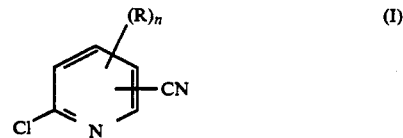

(wherein, R represents an alkyl group, and n represents 0, 1 or 2), such as 2-chloro-3-cyanopyridine, 2-chloro-5-cyanopyridine, 2-chloro-4-cyanopyridine, 2-chloro-6-cyanopyridine and said chlorocyanopyridines having alkyl groups as the substituents.

The non-aqueous reaction system in the present invention includes a reaction system wherein no water is present, and a reaction system wherein water is present in such an extent that the object of the present invention is not impaired.

The solvent used in the present process is a non-aqueous solvent, and there are mentioned, for example, alcohols such as methanol, ethanol and the like; hydrocarbons such as benzene, toluene, cyclohexane and the like; and cyclic ethers such as tetrahydrofuran, dioxane and the like. An alcohol type solvent is particularly preferable in view of the yield of desired product. The solvent is used in an amount of preferably 1–5 times (by weight) based on the starting material, i.e., a cyanopyridine having a chlorine atom at the α-position.

As to the tertiary amine used in the present process there are mentioned aliphatic tertiary amines such as trimethylamine, triethylamine, tributylamine, diisopropylethylamine, tetramethylethylenediamine, tetramethylhexamethylenediamine and the like; aromatic tertiary amines such as N,N'-dimethylbenzylamine and the like; and heterocyclic compounds such as N-methylpyrrolidine and the like. Of these tertiary amines, an aliphatic tertiary amine is preferable in view of the yield of desired product. The tertiary maine is used in an amount of preferably 1–20% by weight based on the starting material, i.e., a cyanopyridine having a chlorine atom at the α-position. Addition of the tertiary amine can depress the dechlorination reaction and other side reactions, increasing the yield of the desired product of the present invention.

Conducting the catalytic reduction of the present invention with ammonia being allowed to coexist in the reaction system, is effective to prevent the undesirable dimerization reaction of the desired product formed in the reaction system, i.e. an aminomethylpyridine having a chlorine atom at the α-position. Ammonia is used in an amount of preferably 20-200% by weight based on the starting material, i.e., a cyanopyridine having a chlorine atom at the α-position. Ordinarily, used of ammonia in the same amount as that of the starting material is effective in view of the reaction efficiency.

As to the hydrogenation catalyst used in the present process, there are mentioned those ordinarily used in catalytic reduction. Specific examples include Raney catalysts such as Raney nickel, Raney cobalt and the like; and noble metal catalysts such as palladium-carbon, ruthenium-carbon, rhodium-carbon, platinum-carbon and the like. A Raney nickel is particularly preferable in view of the yield of desired product. Since use of a large mount of the catalyst accelerates not only the desired catalytic reduction but also a dechlorination reaction, the preferable amount of catalyst used is 1-30% by weight based on the starting material, i.e., a cyanopyridine having the chlorine atom at α-position.

It is important that the reaction temperature employed in the present process be relatively low in order to depress the dechlorination reaction. A preferable reaction temperature is 0°-60° C., and more preferably 20°-50° C. in view of the reaction rate.

The reaction procedure used in the present process is not particularly restricted. In an ordinary procedure, there are fed, into a high-pressure reactor, a starting material (a cyanopyridine having a chlorine atom at the α-portion), a hydrogenation catalyst, a non-aqueous solvent and, as necessary, a tertiary amine and ammonia; then the mixture is heated; and a reaction is conducted while introducing, whenever necessary, hydrogen gas in an amount consumed in the reaction. It is also possible that a reaction can be conducted while feeding under pressure, into the reaction system, a starting material (a cyanopyridine having a chlorine atom at the α-position) dissolved in a non-aqueous solvent.

In a preferred embodiment of the present invention, there are fed, into an autoclave, the starting material (a cyanopyridine having a chlorine atom at the α-position), a non-aqueous solvent, a tertiary amine, a hydrogenation catalyst and ammonia; they are slowly heated while introducing hydrogen gas thereinto; and a reaction is conducted while keeping the abovementioned reaction temperature and feeding hydrogen gas at a normal pressure or above, preferably 3-10 atm. Hydrogen absorption is over in 1-3 hours after hydrogen introduction, whereby the starting material (a cyanopyridine having the chlorine atom at α-position) is completely consumed and the reaction is over. When ammonia is used in a large amount, the reaction pressure exceeds the above upper limit (10 atm.) and reaches, for example, 40 atom. or above; however, the catalytic reduction of the present invention can achieve the object of the present invention even at such a high reaction pressure.

The separation and purification of the desired product (an aminomethylpyridine having a chlorine atom at the α-position) formed in the present process, can be easily conducted by filtering off catalyst from reaction mixture, distilling away solvent from filtrate, and subsequently distilling residue.

EXAMPLES

The present invention is described more specifically by the following Examples. However, the present invention is by no means restricted to the Examples alone.

EXAMPLE 1

Into an autoclave having 1 liter capacity of electromagnetic mixing type were fed 100 g of 6-chloro-5-cyanopyridine, 300 g of methanol, 20 g of a Raney nickel and 100 g of ammonia. Then, hydrogen gas was introduced thereinto and the reaction system has heated, whereby the temperature and pressure of the system were elevated to 40° C. and to 8 atm., respectively, after which a catalytic reduction was conducted at said temperature and said pressure while continuing the feeding of hydrogen. The absorption of hydrogen was over in 1 hour after hydrogen gas introduction.

After the completion of the reaction, the autoclave was cooled to room temperature; the reaction mixture was filtered to remove the catalyst; the filtrate was subjected to evaporation to remove ammonia, methanol, etc.; the residue was distilled to obtain 65.6 g (yield: 63.7%) of 2-chloro-5-aminomethylpyridine and 14.9 g (yield: 9.1%) of 3-picolyamine.

Boiling point of 2-chloro-5-aminomethylpyridine: 100°-105° C./3 mmHg

EXAMPLE 2

A reaction and a post-treatment were conducted in the same manners as shown in Example 1 except that 2-chloro-4-cyanopyridine was used in place of 2-chloro-5-cyanopyridine, whereby 75.2 g (yield: 73.1%) of 2-chloro-4-aminomethylpyridine and 6.5 g (yield: 8.4%) of 4-picolylamine were obtained.

COMPARATIVE EXAMPLE

A reaction and a post-treatment were conducted in the same manners as shown in Example 1 except that a mixed solvent consisting of 300 g of methanol and 60 g of water was used as a solvent in place of 300 g of methanol, whereby 49.2 g (yield: 47.8%) of 2-chloro-5-aminomethylpyridine and 13.4 gg (yield: 17.2%) of 3-picolylamine were obtained.

EXAMPLE 3

A reaction and a post-treatment were conducted in the same manners as shown in Example 1 except that 5 g of triethylamine was allowed to coexist, whereby 80.6 g (yield: 78.3%) of 2-chloro-5-aminomethylpyridine and 3.2 g (yield: 4.1%) of 3-picolylamine were obtained.

EXAMPLE 4

A reaction and a post-treatment were conducted in the same manners as shown in Example 1 except that diisopropylethylamine was used as a tertiary amine in place of triethylamine, whereby 70.0 g (yield: 68.0%) of 2-chloro5-aminomethylpyridine and 4.8 g (yield: 6.2%) of 3-picolylamine were obtained.

EFFECTS OF THE INVENTION

According to the process of the present invention, an aminomethylpyridine having the chlorine atom at α-position, which is a desired product useful as a starting material for pharmaceutical chemicals, agricultural chemicals, and intermediates therefor can be produced at a high yield as compared with conventional processes, by subjecting a starting material, i.e. a cyanopyridine having a chlorine atom at the α-position, to a catalytic reduction in a non-aqueous reaction system.

The aminomethylpyridine having a chlorine atom at the α-position, which is a desired product, can also be produced at a higher yield as compared with conventional processes, by subjecting the starting material, i.e. a cyanopyridine having a chlorine atom at the α-position, to a catalytic reduction with a tertiary amine being allowed to coexist in the reaction system.

I claim:

1. A process for producing an aminomethylpyridine having a chlorine atom at the α-position by subjecting a 2-chlorocyanopyridine represented by the formula (I)

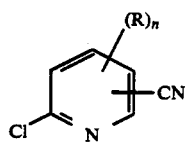

(wherein, R represents an alkyl group, an n represents 0, 1 or 2), to a catalytic reduction in the presence of a hydrogenation catalyst, which process is characterized in that said cyanopyridine is subjected to a catalytic reduction in a non-aqueous reaction system.

2. A process for producing an aminomethylpyridine having a chlorine atom at the α-position by subjecting a 2-chlorocyanopyridine represented by the formula (I)

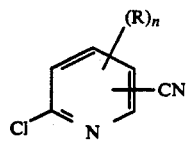

(wherein, R represent an alkyl group and n represents 0, 1 or 2) to catalytic reduction in the presence of a hydrogenation catalyst, which process is characterized in that said cyanopyridine is subjected to a catalytic reduction with a tertiary amine being allowed to coexist in the reaction system.

3. A process according to claim 1, characterized in that an alcohol is used as a solvent.

4. A process according to claim 2, characterized in that the catalytic reducing reaction is conducted in a non-aqueous system.

5. A process according to claim 4, characterized in that an alcohol is used as a solvent.

6. A process according to claim 2, wherein the tertiary amine is an aliphatic tertiary amine.

7. A process according to claim 3, wherein the hydrogenation catalyst is a Raney nickel.

8. A process according to claim 6, wherein the hydrogenation catalyst is a Raney nickel.

9. A process according to claim 3, characterized in that the catalytic reduction is conducted in the coexistence of ammonia.

10. A process according to claim 4, characterized in that the catalytic reduction is conducted in the coexistence of ammonia.

* * * * *